(12) United States Patent
Venturini et al.

(10) Patent No.: US 10,028,778 B2
(45) Date of Patent: Jul. 24, 2018

(54) ENDOSSEOUS SCREW ASSEMBLY AND INTERNAL FIXATION SYSTEM COMPRISING SAID ENDOSSEOUS SCREW ASSEMBLY

(71) Applicant: ORTHOFIX S.R.L., Bussolengo (Verona) (IT)

(72) Inventors: Daniele Venturini, Povegliano Veronese (IT); Denis Lorenzini, Caprino Veronese (IT)

(73) Assignee: Orthofix S.R.L., Verona (IT)

( * ) Notice: Subject to any disclaimer, the term of this patent is extended or adjusted under 35 U.S.C. 154(b) by 0 days.

(21) Appl. No.: 15/035,956

(22) PCT Filed: Nov. 11, 2014

(86) PCT No.: PCT/IB2014/002413
§ 371 (c)(1),
(2) Date: May 11, 2016

(87) PCT Pub. No.: WO2015/068027
PCT Pub. Date: May 14, 2015

(65) Prior Publication Data
US 2016/0296260 A1    Oct. 13, 2016

(30) Foreign Application Priority Data

Nov. 11, 2013    (EP) ..................................... 13192344

(51) Int. Cl.
*A61B 17/70*    (2006.01)
*A61B 17/72*    (2006.01)
(Continued)

(52) U.S. Cl.
CPC ........ *A61B 17/725* (2013.01); *A61B 17/1721* (2013.01); *A61B 17/1728* (2013.01);
(Continued)

(58) Field of Classification Search
CPC . A61B 17/72; A61B 17/7291; A61B 17/7233; A61B 17/7241; A61B 17/7225; A61B 17/725; A61B 17/164
(Continued)

(56) References Cited

U.S. PATENT DOCUMENTS 4,617,922 A * 10/1986 Griggs ................. A61B 17/746
606/104
5,976,139 A * 11/1999 Bramlet ............. A61B 17/1659
606/282
(Continued)

FOREIGN PATENT DOCUMENTS

| WO | 01/74261 A1 | 10/2001 |
| WO | 2012/099944 A1 | 7/2012 |
| WO | 2013/075730 A1 | 5/2013 |

OTHER PUBLICATIONS

International Search Opinion, PCT/IB2014/002413, dated May 11, 2015, 6 pages.
(Continued)

*Primary Examiner* — Eduardo C Robert
*Assistant Examiner* — Tara R Carter
(74) *Attorney, Agent, or Firm* — Baker & McKenzie LLP

(57) ABSTRACT

An endosseous screw assembly (100) for an internal fixation system (SC; SP), whose connection to the rest of the system is unusually easy for the surgeon, comprising: a longitudinally extending rod (1) equipped with at least one threaded proximal portion (2); a connection sleeve (3), within which a portion of the rod (1) is slidingly guided, said connection sleeve (3) being arranged to be inserted into a connection hole of an internal fixation member by snap-connecting within said connection hole up to reach a locking position; said rod (1) and said connection sleeve (3) comprising such mutual engagement means so as to form an axial constraint to the sliding of the rod (1) into the connection sleeve (3), (Continued)

so as to define, when the threaded proximal portion (2) advances into a bone site of the patient, a dragging of the connection sleeve (3) into the connection hole up to reach the locking position.

10 Claims, 25 Drawing Sheets

(51) Int. Cl.
*A61B 17/17* (2006.01)
*A61B 17/74* (2006.01)
*A61B 17/86* (2006.01)
*A61B 17/88* (2006.01)
*A61B 17/80* (2006.01)

(52) U.S. Cl.
CPC .......... *A61B 17/1742* (2013.01); *A61B 17/72* (2013.01); *A61B 17/744* (2013.01); *A61B 17/746* (2013.01); *A61B 17/808* (2013.01); *A61B 17/8014* (2013.01); *A61B 17/8057* (2013.01); *A61B 17/863* (2013.01); *A61B 17/864* (2013.01); *A61B 17/8615* (2013.01); *A61B 17/8635* (2013.01); *A61B 17/8685* (2013.01); *A61B 17/8897* (2013.01); *A61B 17/8038* (2013.01); *A61B 17/8066* (2013.01); *A61B 17/8625* (2013.01)

(58) Field of Classification Search
USPC ...................................................... 606/62–68
See application file for complete search history.

(56) References Cited

U.S. PATENT DOCUMENTS

| 2008/0119856 | A1* | 5/2008 | Gotfried | .............. | A61B 17/744 |
| | | | | | 606/67 |
| 2008/0281326 | A1* | 11/2008 | Watanabe | ............ | A61B 17/164 |
| | | | | | 606/62 |
| 2009/0254129 | A1 | 10/2009 | Tipirneni et al. | | |

OTHER PUBLICATIONS

Written Opinion of the International Searching Authority, PCT/IB2014/002413, dated May 11, 2015, 10 pages.
International Preliminary Report on Patentability, dated Oct. 12, 2015, 6 pages.

* cited by examiner

ENDOSSEOUS SCREW ASSEMBLY AND INTERNAL FIXATION SYSTEM COMPRISING SAID ENDOSSEOUS SCREW ASSEMBLY

FIELD OF APPLICATION

The present invention relates to the field of orthopedic surgery and it relates to an endosseous screw assembly, particularly of the type used in internal fixation systems comprising plates or nails.

The invention also relates to the internal fixation system comprising said endosseous screw assembly.

PRIOR ART

Internal fixation systems, widely used in the orthopedic field, comprise different types of endosseous implants generally applied to stabilize the fractured bone site of a patient.

Internal fixation systems can comprise a bone plate, which is fixed in contact with an external surface of the fractured bone in order to ensure the alignment and fixation of two or more segments thereof. In order to allow the plate to be fixed, the system provides in these cases a plurality of endosseous screws crossing as many holes made on the element.

Internal fixation systems can also comprise an endomedullary nail, which is typically inserted into the medullary canal of the long bone of a patient. In this case too, one or more endosseous screws are generally provided, which transversely cross the cortical bone and interface the endomedullary nail in order to stabilize the system.

In both above-described implant types, a stable connection must be realized between the screw rod and the plate or nail body. This connection must be able to discharge on the plate/nail the torsional and bending stress applied to the screw rod, allowing in the meantime the controlled axial sliding of the rod itself in order to allow screwing and removal operations.

In order to meet said requirements, connection systems known in the art are generally quite elaborated and complex, thus defining a critical step—both from the time point of view and from the point of view of the attention required by the surgeon—of the implantation of the fixation system.

By way of example, mention is made of the prior art patent applications US 2008/0119856 and WO 2013/075730. The suggested methods for inserting and connecting the screws to the endomedullary nail and/or plate provide the following use of a plurality of specific instruments, or a sequence of screwings on different components kept apart from each other. As a clear result, the screw insertion step in the prior art methods shown requires much attention and a quite long time to the surgeon charged of implanting the internal fixation system.

The technical problem underlying the present invention is therefore to provide an endosseous screw assembly and a related internal fixation system allowing both the operations of inserting and stabilizing the screw into the nail/plate, and the opposite operations in case of implant removal to be considerably simplified.

SUMMARY OF THE INVENTION

Said technical problem is solved by an endosseous screw assembly according to claim 1, as well as by an internal fixation system comprising said assembly, according to the text of claim 7.

Further features and advantages will become more apparent from the following detailed description of some preferred, but not exclusive, embodiments of the present invention, with reference to the attached figures, given by way of not-limiting example.

DETAILED DESCRIPTION

Figure 10:
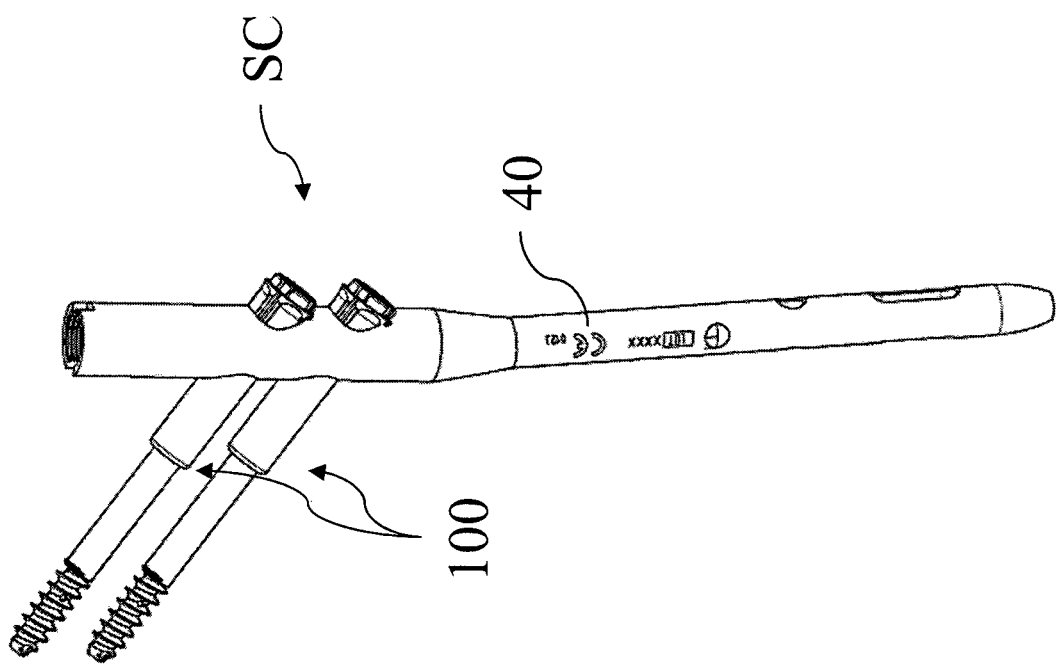
FIG. 10 is a perspective view of a first embodiment of an internal fixation system according to the present invention.
Figure 12:
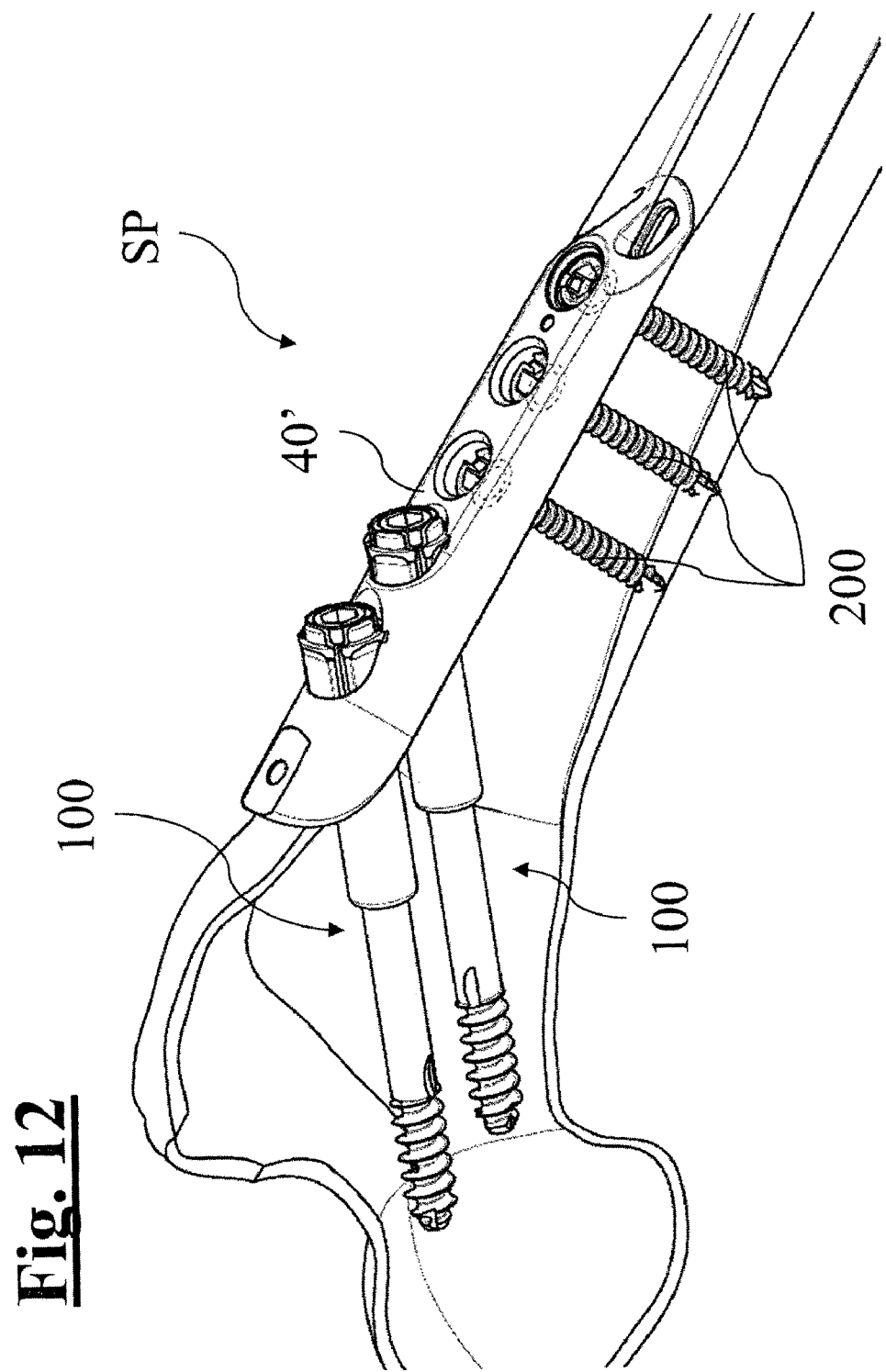
FIG. 12 is a perspective view of a second embodiment of an internal fixation system according to the present invention, implanted on the bone site of a patient.

With reference to the attached figures, and particularly to FIGS. 10 and 12, two internal fixation systems according to a first and second embodiment of the invention have been identified with references SC and SP.

In the first embodiment, shown in FIG. 10, the internal fixation system SC comprises an endomedullary nail 40, particularly a trochanteric nail, and two endosseous screw assemblies 100.

Endosseous screw assemblies 100 are inserted and locked on the trochanteric nail 40, along axes being parallel to each other and inclined compared to the nail axis, and arranged to anchor within the acetabular head of the patient.

In the second embodiment, shown in FIG. 12, the internal fixation system SP comprises a bone plate 40' fixed to the femoral surface of a patient by means of three endosseous screws 200 of the traditional type.

Moreover, the internal fixation system SP provides, in this case too, two endosseous screw assemblies 100 inserted and locked on the bone plate 40', along axes being parallel to each other and skew compared to those of other bone screws 200, and arranged to anchor within the acetabular head of the patient.

Both internal fixation systems SC, SP according to the present invention share a similar fixation system of the endosseous screw assemblies 100 to the internal fixation member, be it the endomedullary nail 40 or the bone plate 40'.

The endosseous screw assemblies 100 used in said two embodiments are in fact the same, and both internal fixation members 40; 40' provide a same connection hole to lock them.

Figure 11:
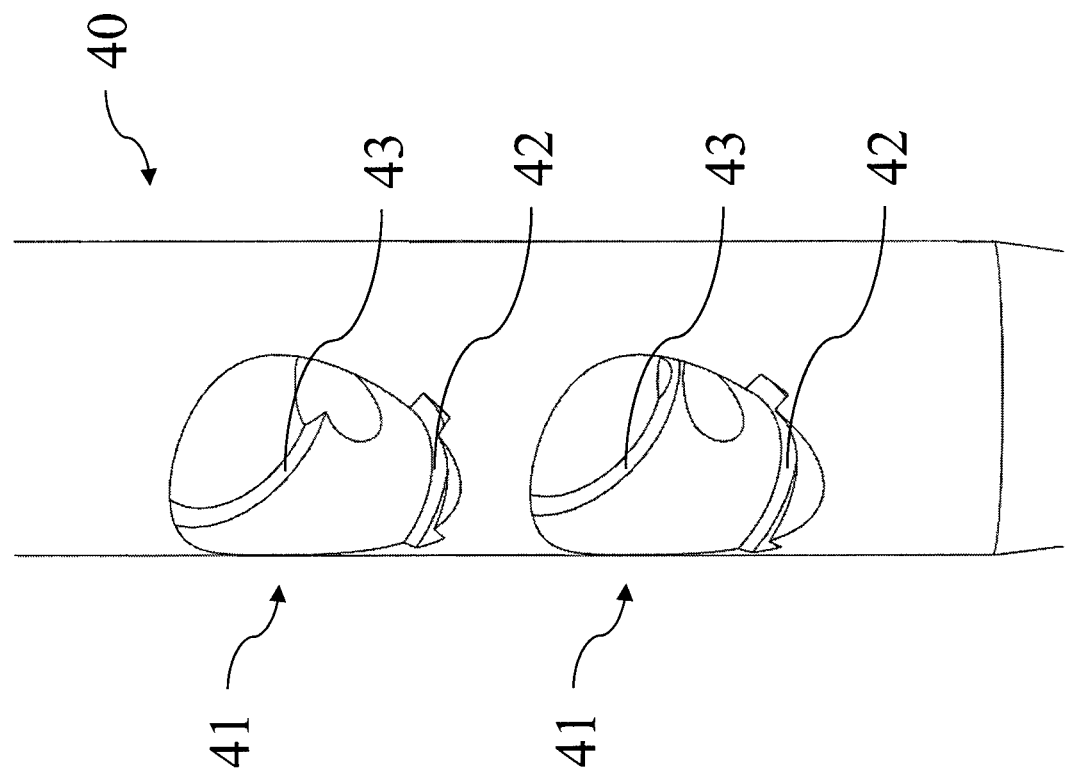
FIG. 11 is a perspective view of a detail of an endomedullary nail belonging to the internal fixation system of FIG. 10.
Figure 18:
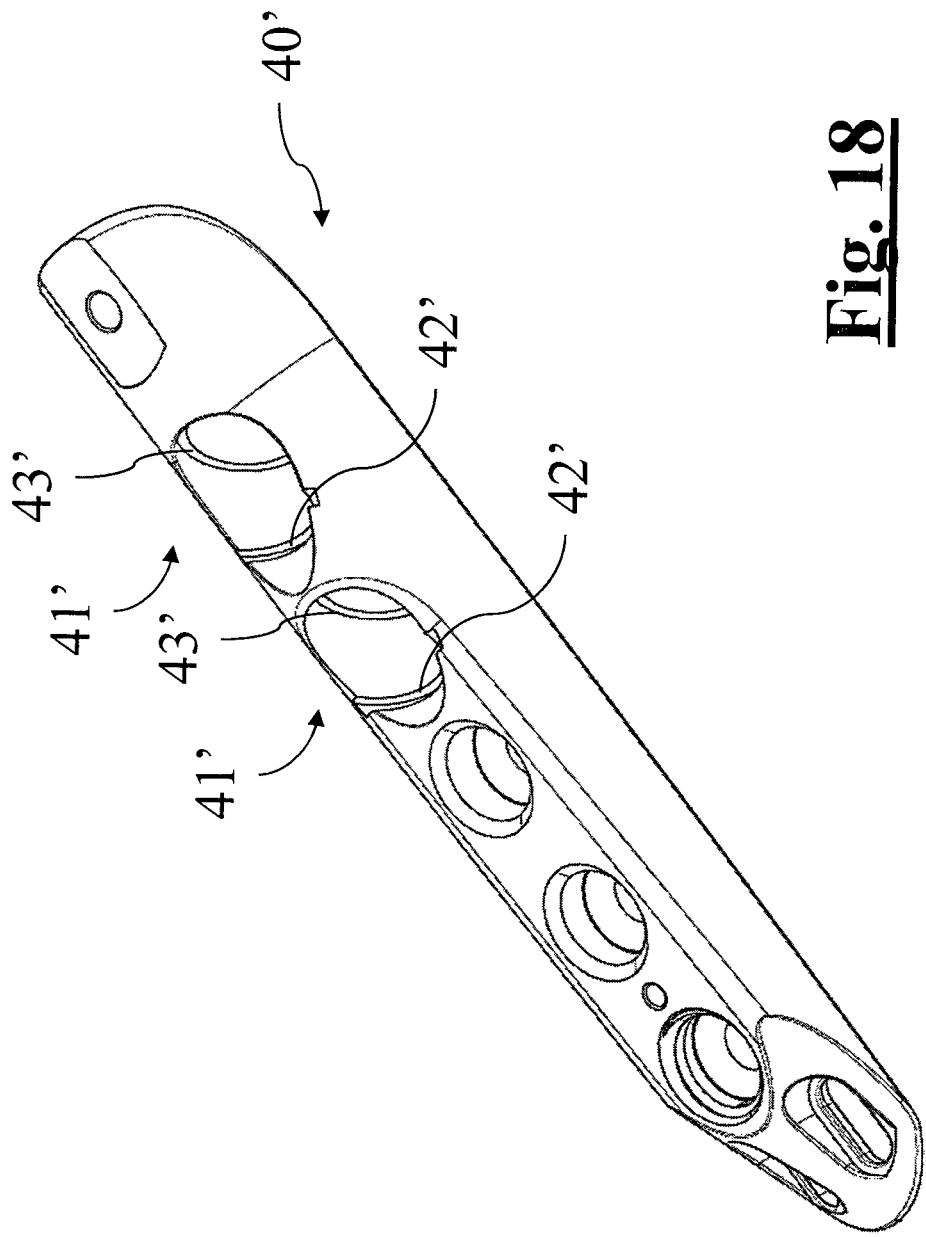
FIG. 18 is a perspective view of a bone plate belonging to the internal fixation system of FIG. 12.

Connection holes 41; 41', which can be seen in FIG. 11 for the endomedullary nail 40 and in FIG. 18 for the bone plate 40', are generally described hereafter. The description applies without distinction to the endomedullary nail and to the bone plate; it must be noted that, in the figure, the elements related to the bone plate have been identified with the same numeral reference as the endomedullary nail adding the first-index.

Each connection hole 41; 41' has two following portions with a different diameter, which define between them a shoulder 43; 43'. The portion having the greater diameter is naturally turned towards the side of insertion of the endosseous screw assembly 100. On the internal surface thereof a groove 42; 42' is obtained, which extends circumferentially up to meet the outward outlet of the connection hole 41; 41'.

Figure 1:
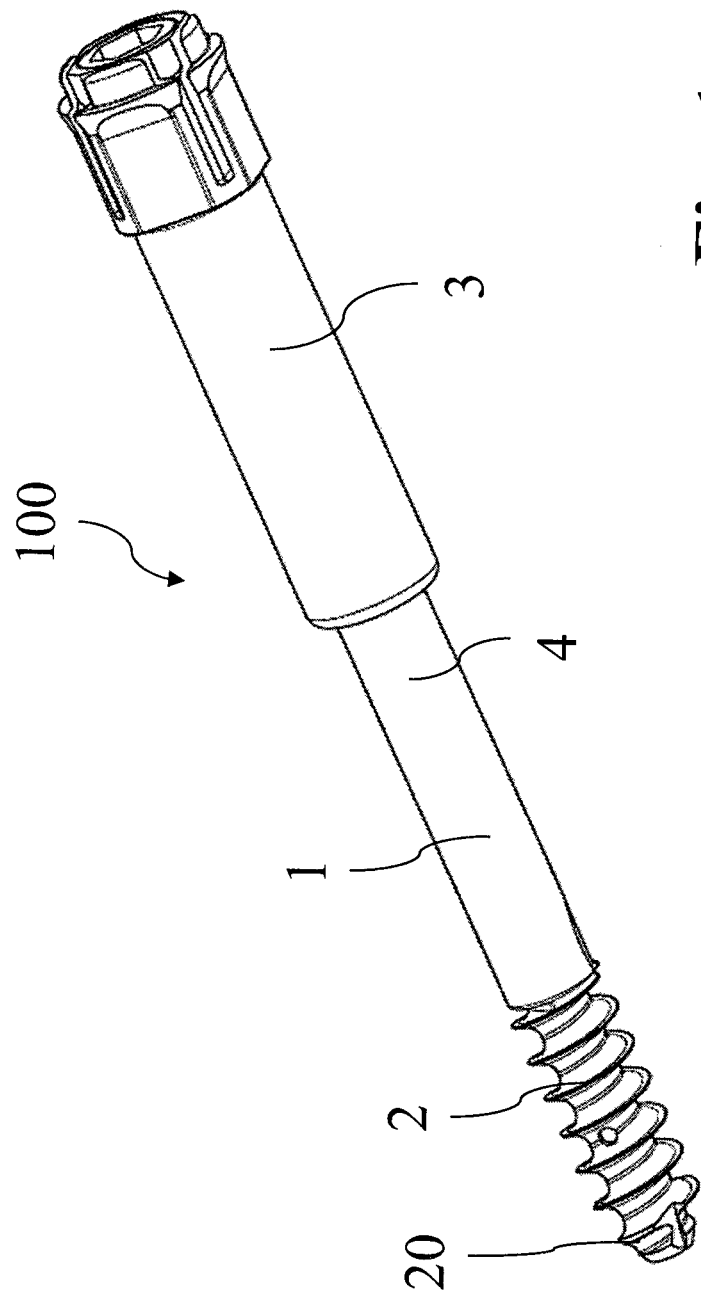
FIG. 1 is a perspective view of an endosseous screw assembly according to the present invention, wherein a screw rod and a connection sleeve are arranged in a first relative position.
Figure 2:
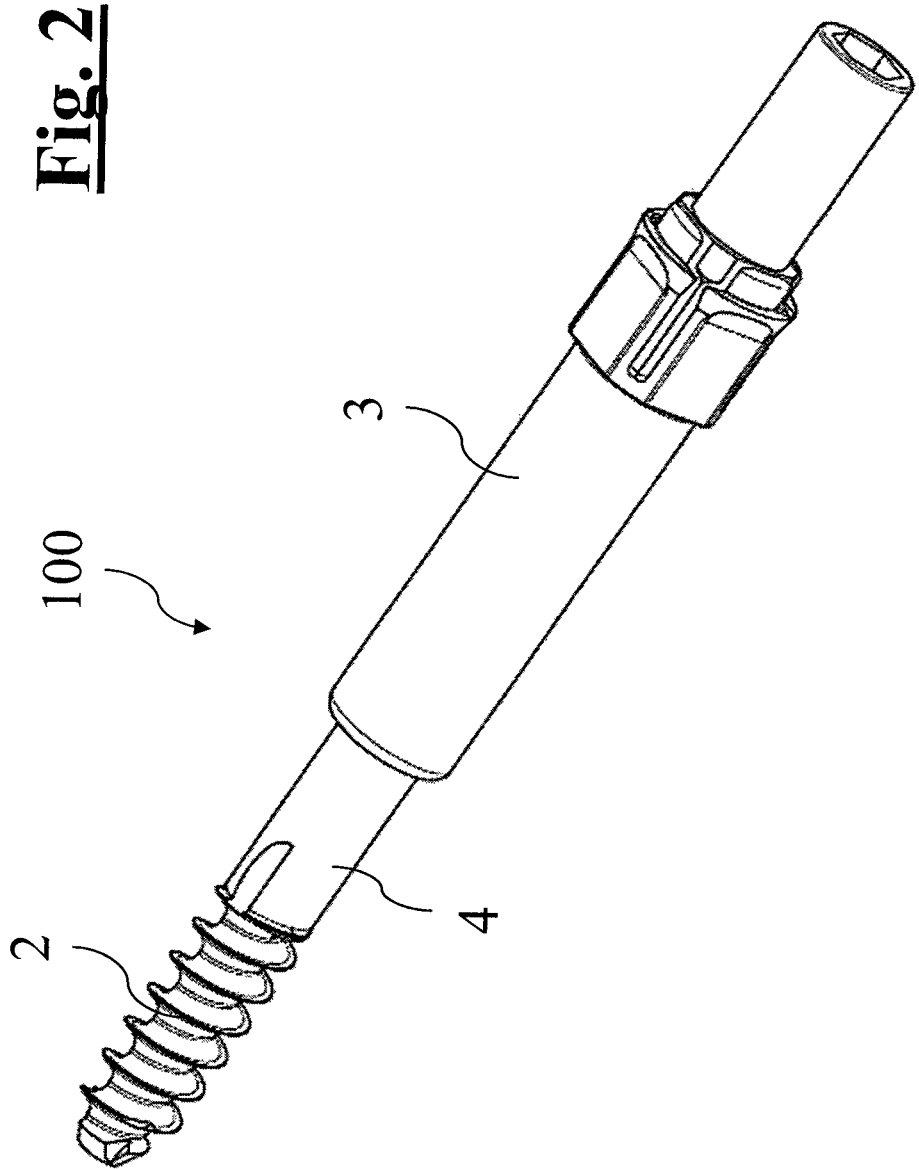
FIG. 2 is a perspective view of the endosseous screw assembly of FIG. 1, wherein the rod and the connection sleeve are arranged in a second relative position.
Figure 3:
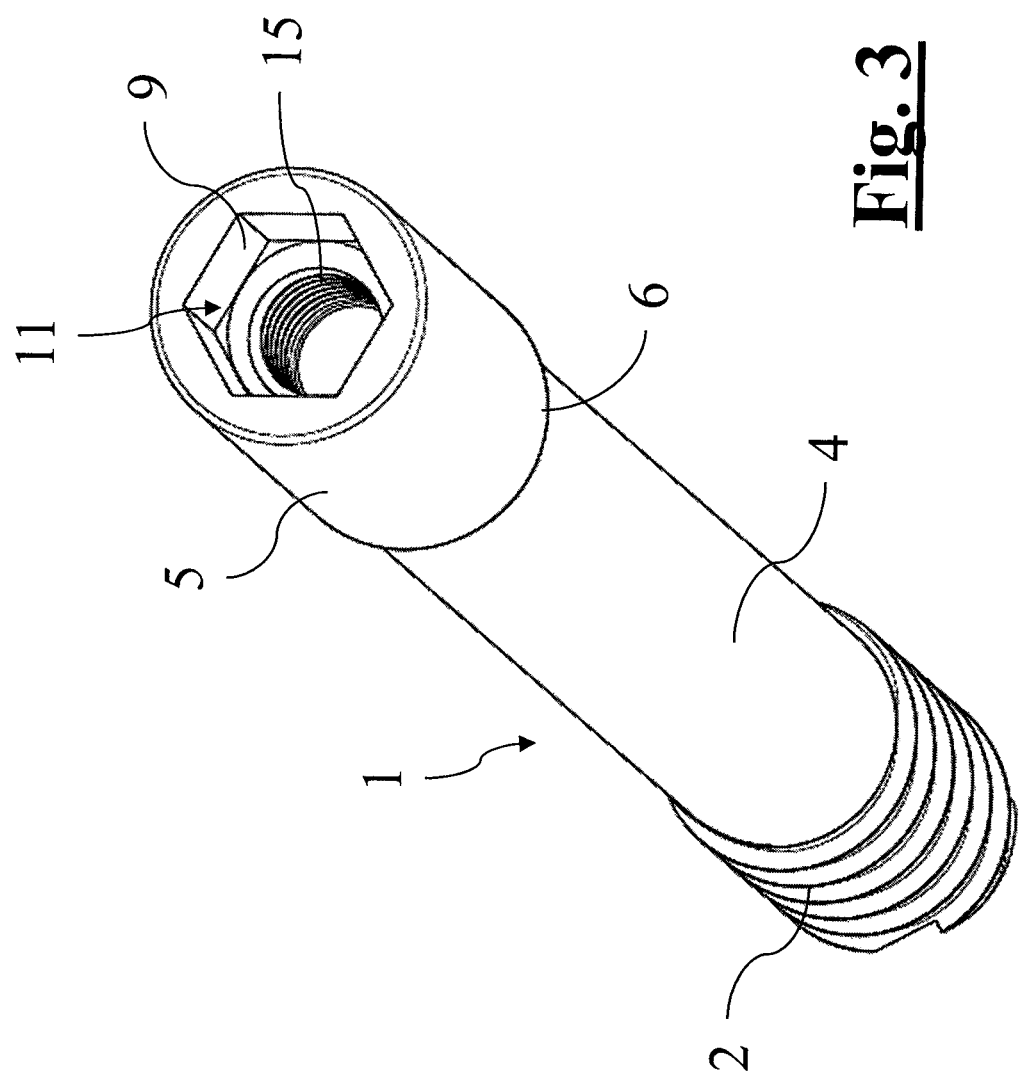
FIG. 3 is a perspective view of the sole rod belonging to the endosseous screw assembly of FIG. 1.
Figure 4:
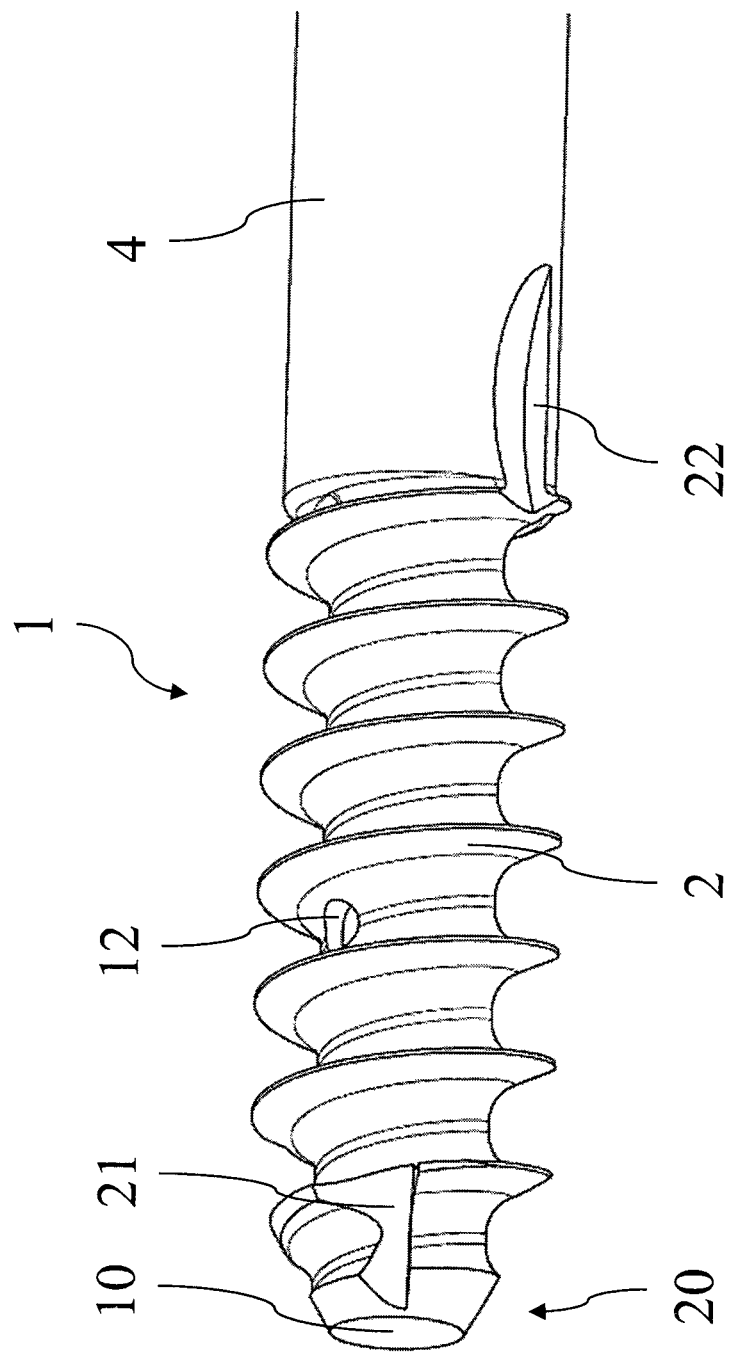
FIG. 4 is a perspective view of a detail of the rod of FIG. 3.
Figure 5:
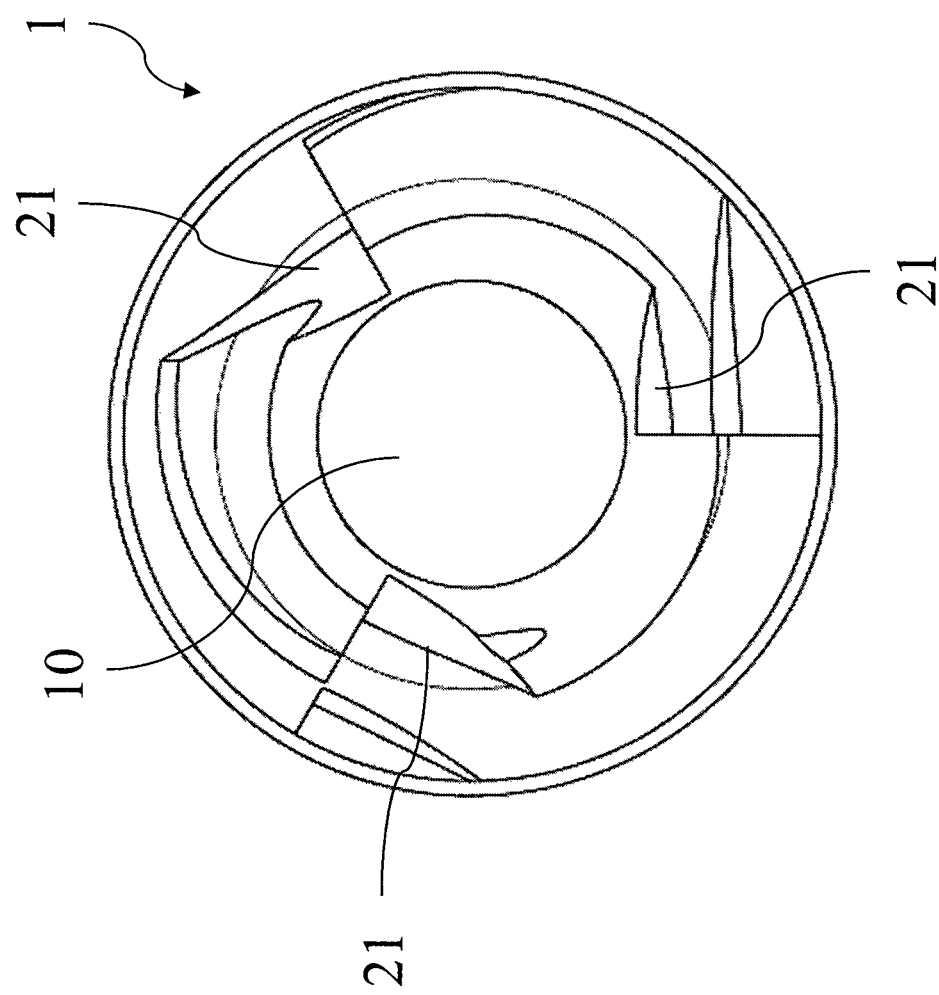
FIG. 5 is a front view of the rod of FIG. 3.
Figure 6:
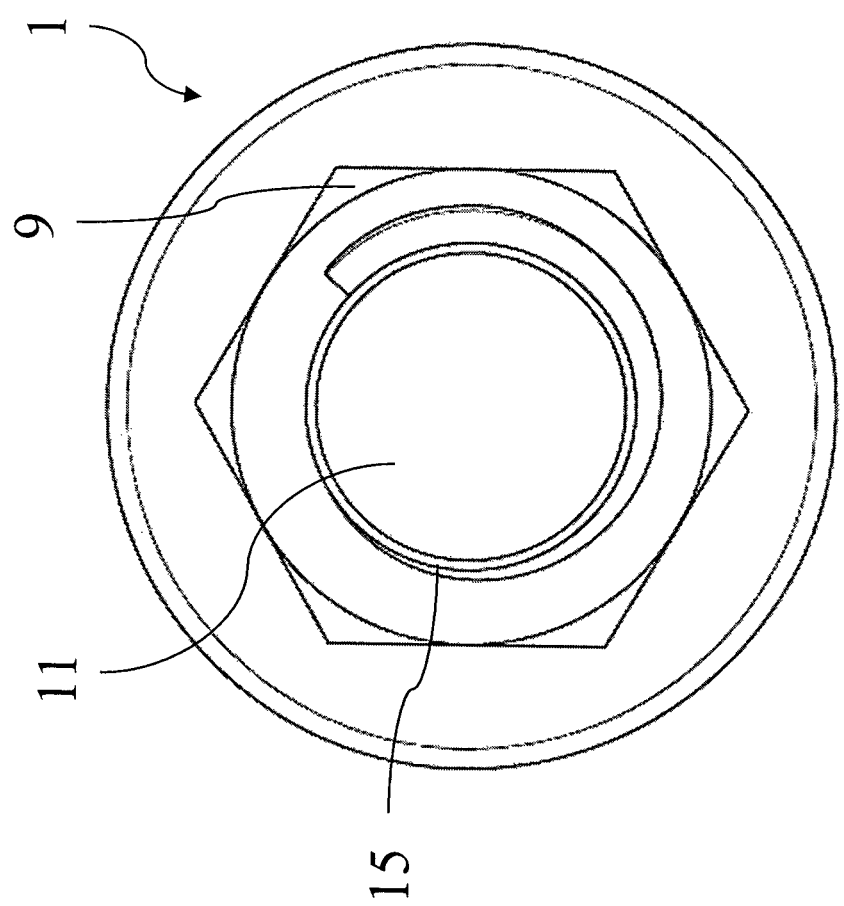
FIG. 6 is a back view of the rod of FIG. 3.

The endosseous screw assembly 100, globally illustrated in FIGS. 1 and 2, comprises two elements being coupled but structurally distinct: a longitudinal rod 1 and a connection sleeve 3.

The rod 1 of the endosseous screw assembly 100, individually illustrated in FIGS. 3-6, comprises a threaded proximal portion 2, a following cylindrical intermediate portion 4 and finally a distal portion 5, which is also cylindrical, but with a greater diameter.

In the embodiment here described, the whole rod 1 is cannulated, i.e. it has an axial passage connecting a distal opening 11 to a proximal opening 10. This solution allows a guide wire to be used to facilitate the insertion step of the endosseous screw assembly 100; moreover the axial passage can advantageously define an access way to inject in situ a bone substitute or other biological substances.

The threaded proximal portion 2 is arranged to penetrate into the bone site of the patient, and it is particularly equipped with a self-drill bit 20 that allows the screw to proceed into the bone. The bit 20 provides a plurality of circumferentially equidistant notches 21, three in the embodiment being presently illustrated, which facilitate the self-drilling and tapping step of the screw within the bone site. Moreover the proximal opening 10 of said axial passage opens in correspondence with the bit 20.

It must be noted that the external diameter of the thread of the proximal portion 2 is slightly greater than the diameter of the cylinder which forms the intermediate portion 4, so as to axially constrain the connection sleeve 3 sliding along the rest of the rod 1.

A radial notch 22 extending along the external surface of the intermediate portion 4 is provided in correspondence with the thread interruption; said radial notch 22 increases the resistance to accidental unscrewing.

One or more radial holes 12, communicating with the above-mentioned axial passage, open on the external surface of the threaded proximal portion 2, particularly in correspondence with a thread bottom. These radial holes 12 allow the radial extrusion surface and the diffusion of a possible bone substitute to be increased.

The intermediate portion 4 and the distal portion 5 of the rod, as said above, are both cylindrical, but with a diameter increase in the distal part. It must be noted in particular how the diameter variation defines a shoulder serving as an axial clamp 6 for the connection sleeve 3 which slides above the rod 1, according to modes described hereafter.

The distal opening 11 of the axial passage opens in correspondence with the free end of the distal portion 5, as mentioned above.

That distal opening 11 provides a first cavity which defines a sunken housing 9, in the present example being hexagon-shaped, which allows an instrument to screw the rod 1 to be engaged.

Always within the distal opening, deeply compared to the sunken housing 9, an internal thread 15 is provided, which allows the possible attachment of an injection instrument or a plug or piston within the rod.

Figure 25:
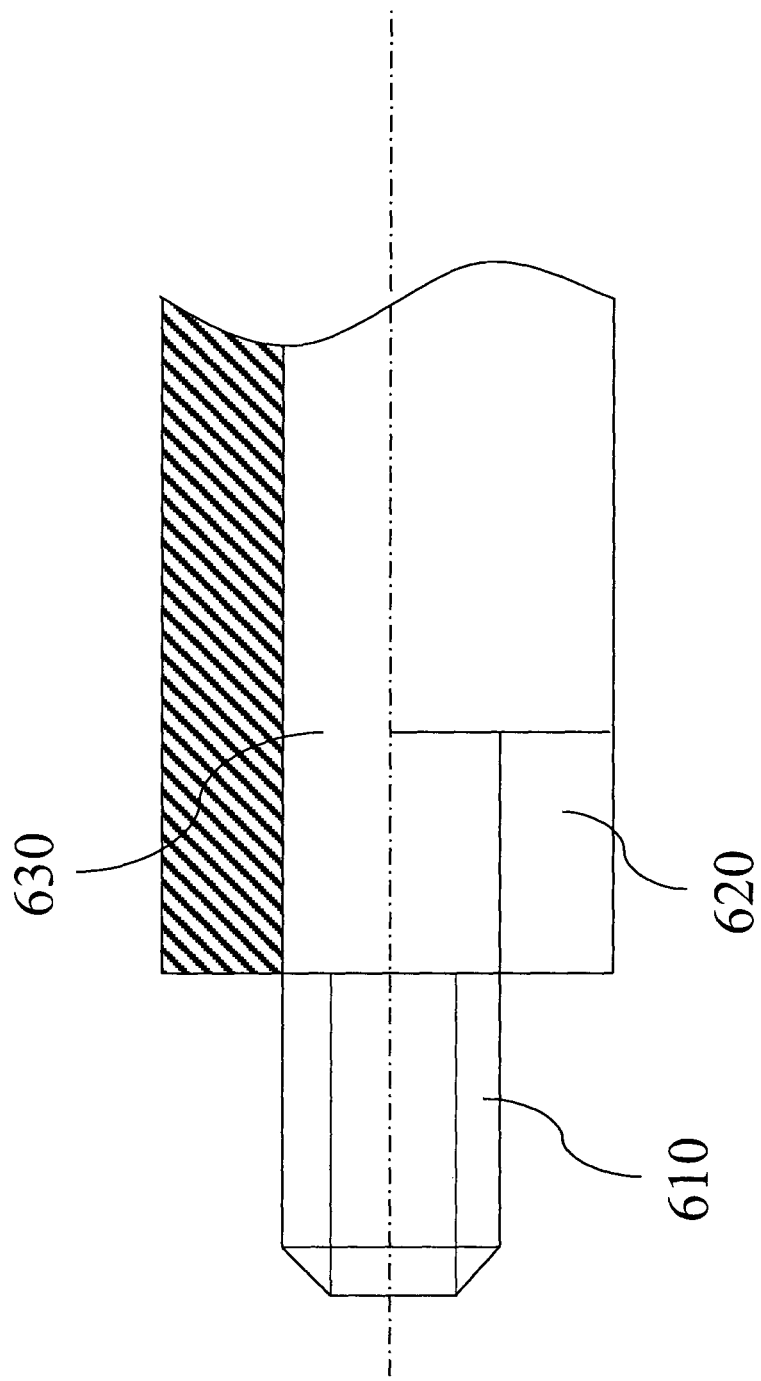
FIG. 25 shows a detail in partial section of an instrument used to remove an internal fixation system according to the present invention.

Moreover the internal thread 15 allows the rod 1 to be connected to a suitable cannulated screwdriver, equipped with an external-thread bar 610 axially constrained with the screwdriver itself, if the removal of the rod 1 is difficult. A detail of that screwdriver bit is shown in the attached FIG. 25: the external-thread bar 610 precedes the hexagonal head 620 defining an axial abutment, while the instrument body provides an internal cannula 630.

Figure 7:
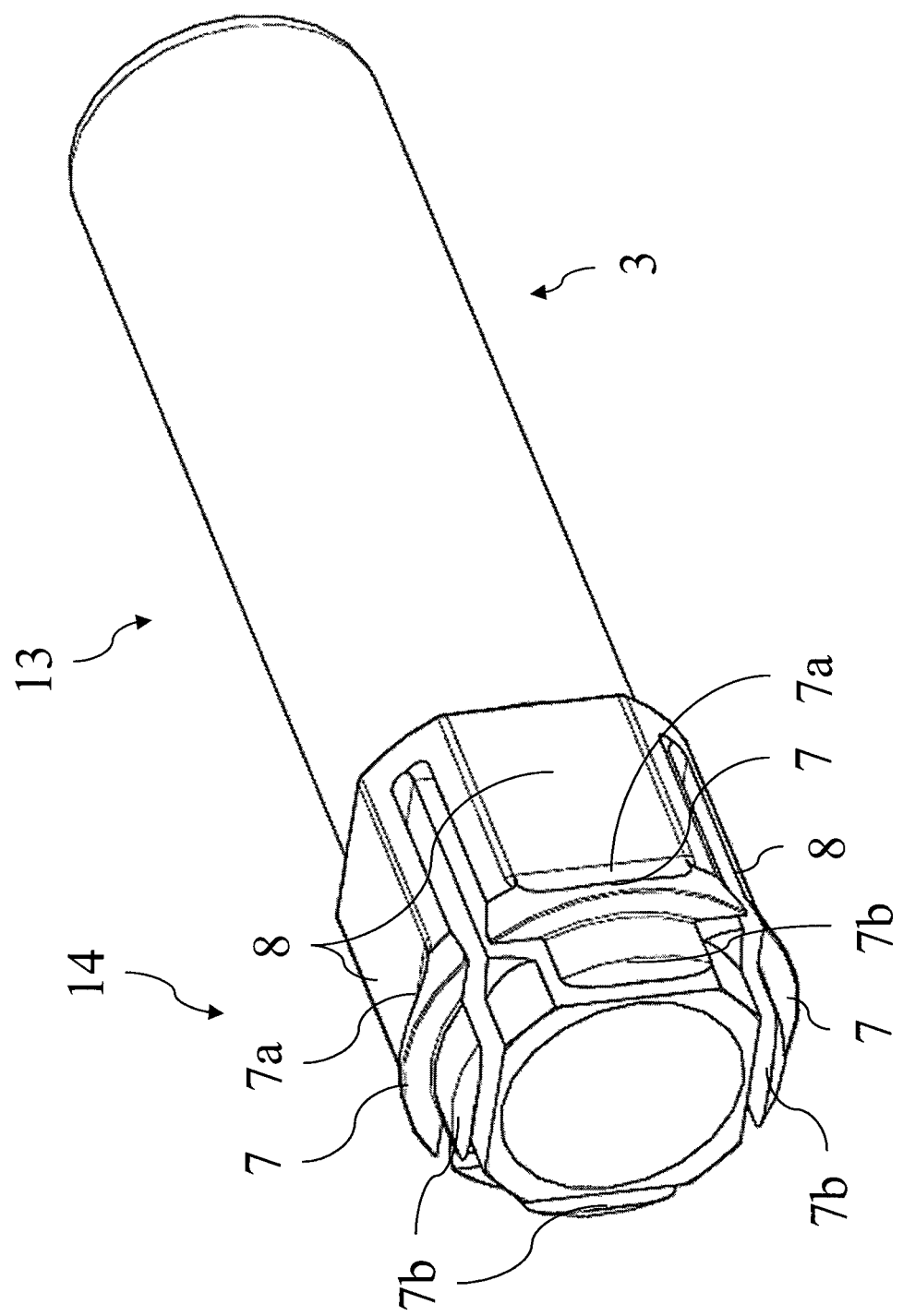
FIG. 7 is a perspective view of the sole connection sleeve belonging to the endosseous screw assembly of FIG. 1.
Figure 8:
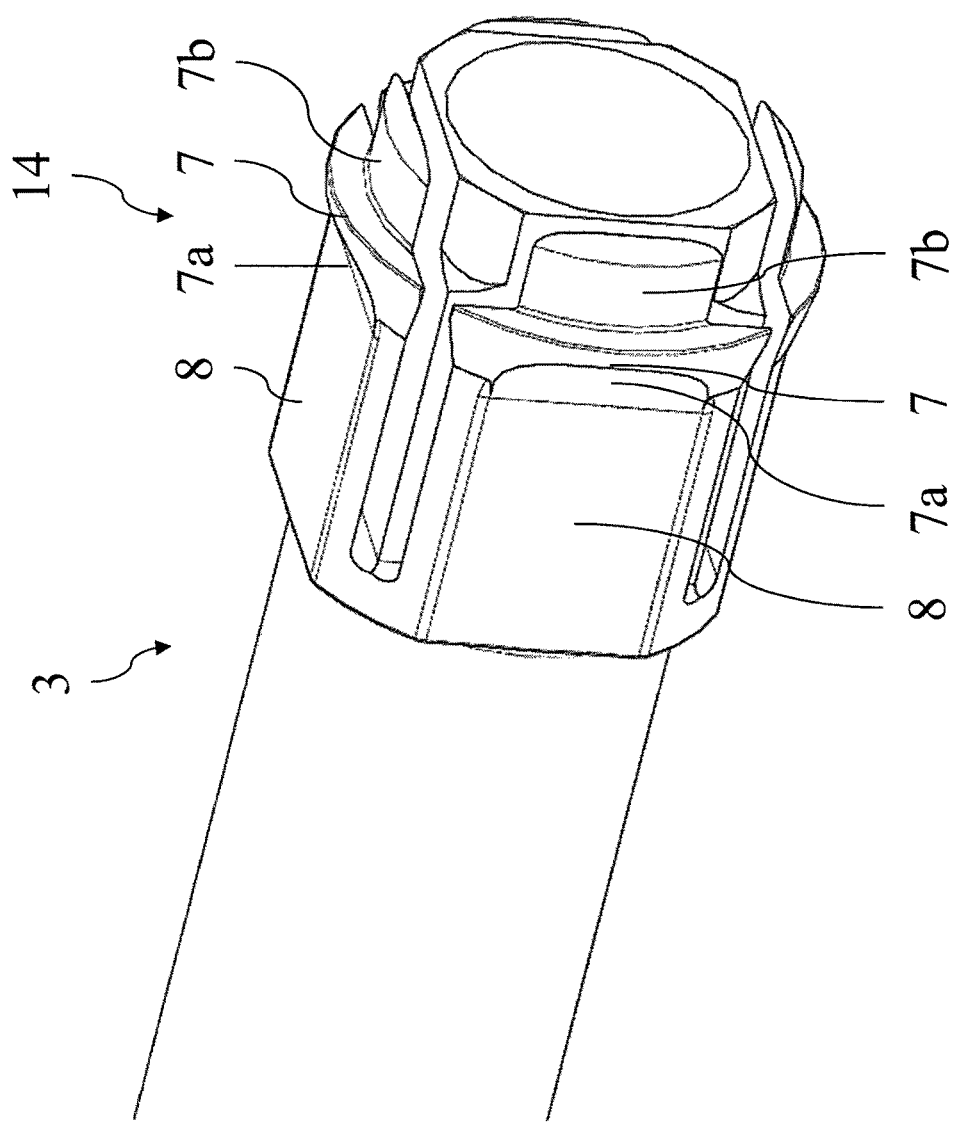
FIG. 8 is a perspective view of a detail of the connection sleeve of FIG. 7.
Figure 9:
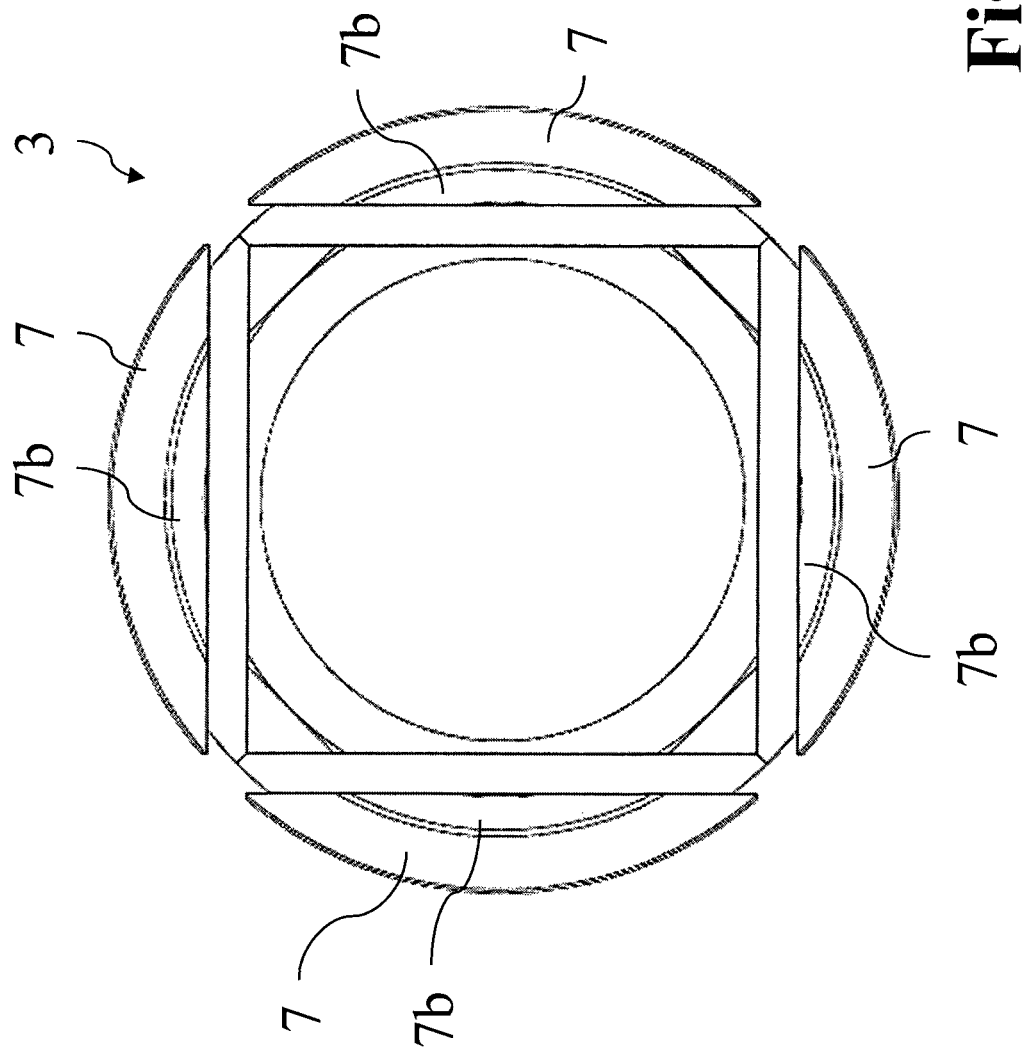
FIG. 9 is a back view of the connection sleeve of FIG. 7.

The connection sleeve 3, individually illustrated in FIGS. 7-9, is slidingly associated to the intermediate 4 and distal 5 portions of the rod 1, as it can be inferred through the comparison of the relative position of the sleeve itself in FIGS. 1 and 2.

The sliding of the connection sleeve 3 is axially constrained in both directions: in the proximal direction by the external diameter of the thread; in the distal direction by the above-identified axial clamp 6.

It must be noted in particular how, in the present embodiment, the axial clamp 6 locks the connection sleeve 3 by abutting against an internal element of the connection sleeve 3 itself. By way of example, the internal abutting element can be realized by plastic deformation of the end part of the connection sleeve 3. Therefore, in the limit stop position identified in FIG. 1, the distal portion 5 of the rod 1 is completely inserted into the connection sleeve 3, and the distal ends of the sleeve and of the rod are arranged at level.

The connection sleeve 3 comprises a proximal cylindrical portion 13 and a distal collar 14.

While inserting the connection sleeve 3 into the respective internal fixation member 40; 40', the proximal cylindrical portion 13 is inserted in guided engagement into the smaller-diameter portion of the connection hole 41; 41', until the distal collar 14 abuts against the above-defined shoulder 43; 43' in a system locking position.

The distal collar 14 provides snap-connection means, described hereafter, arranged for stable engagement in the groove 42; 42' of the connection hole 41; 41' in said locking position.

The distal collar 14, with a prismatic or cylindrical shape, has an external diameter being substantially equal to the diameter of the greater-diameter portion of the connection hole 41; 41'. Tangential cuts are made in the body thickness, which define four brackets 8, joined to the connection sleeve 3 only in correspondence with the proximal end thereof.

Since the sleeve is realized out of a flexible material, for example steel or titanium, the brackets 8 are able to bend, so that the free distal end thereof is able to elastically move in the substantially distal direction.

As many clutch claws 7 are defined in correspondence with the free end of the four brackets 8, which define in sequence a circular profile having a diameter substantially equal to the one of the bottom of the groove 42; 42'.

In the proximal direction, the clutch claws 7 are joined to the respective brackets 8 through draft surfaces 7a.

Therefore, when the connection sleeve 3 is inserted into the connection hole 41; 41', a pressure is exerted on the respective draft surfaces 7a, which causes one or more clutch claws 7 to bend, until, once the locking position is reached, the clutch claws are then released within the groove 42; 42' making the two elements screw and plate or screw and nail integral with each other.

Moreover it must be noted how, in correspondence with the free end thereof, the brackets 8 provide release tabs 7b projecting compared to the related clutch claw 7. The four release tabs 7b, which define in sequence a circular profile having a smaller diameter than the one of the clutch claws 7, allow, as it will appear in the following description, the connection sleeves 3 to be disengaged from the respective connection holes 41; 41'.

With reference to the attached FIGS. 13-17, a method for implanting an internal fixation system SP according to the second one of the above-outlined embodiments is now described.

Nevertheless, a person skilled in the art will have no difficulty in adapting the operations described hereafter also to the implantation of an internal fixation system SC according to said first embodiment.

Figure 13:
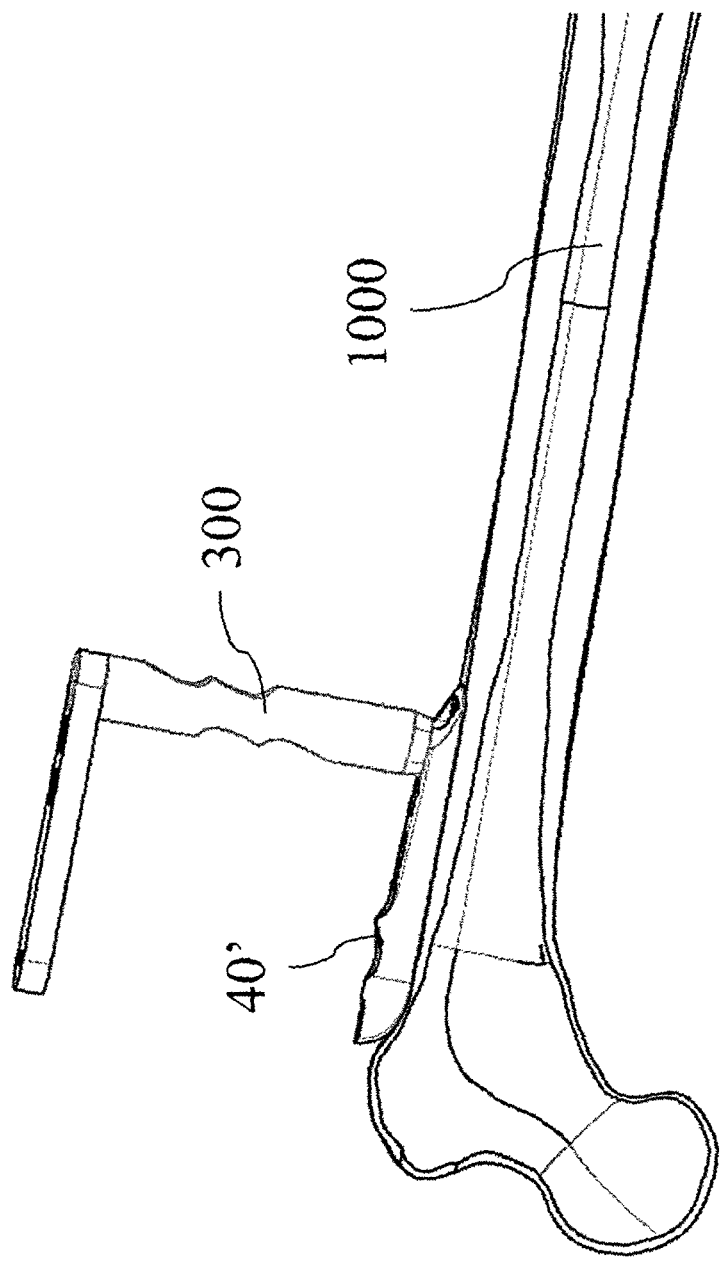
FIGS. 13-17 show following steps of a method for implanting the internal fixation system of FIG. 12.
Figure 21:
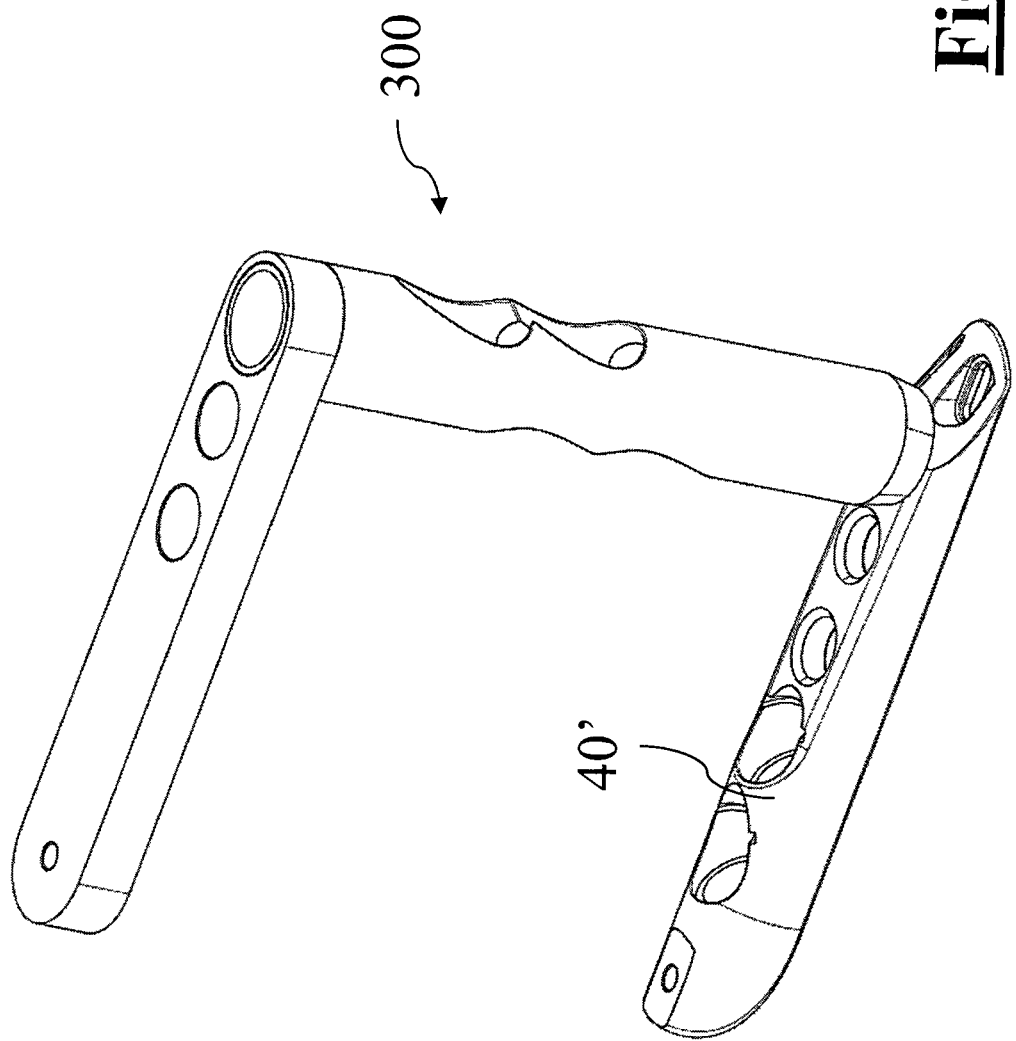
FIGS. 21-24 are perspective views of different instruments used to implant an internal fixation system according to the present invention.

In a first step of the method, illustrated in FIG. 13, the bone plate 40' is inserted in position on the bone 1000—in this case a femur—of a patient, by means of a suitable first surgical guide 300, individually illustrated in FIG. 21.

It must be noted that this operation requires a single incision by the surgeon.

Figure 14:
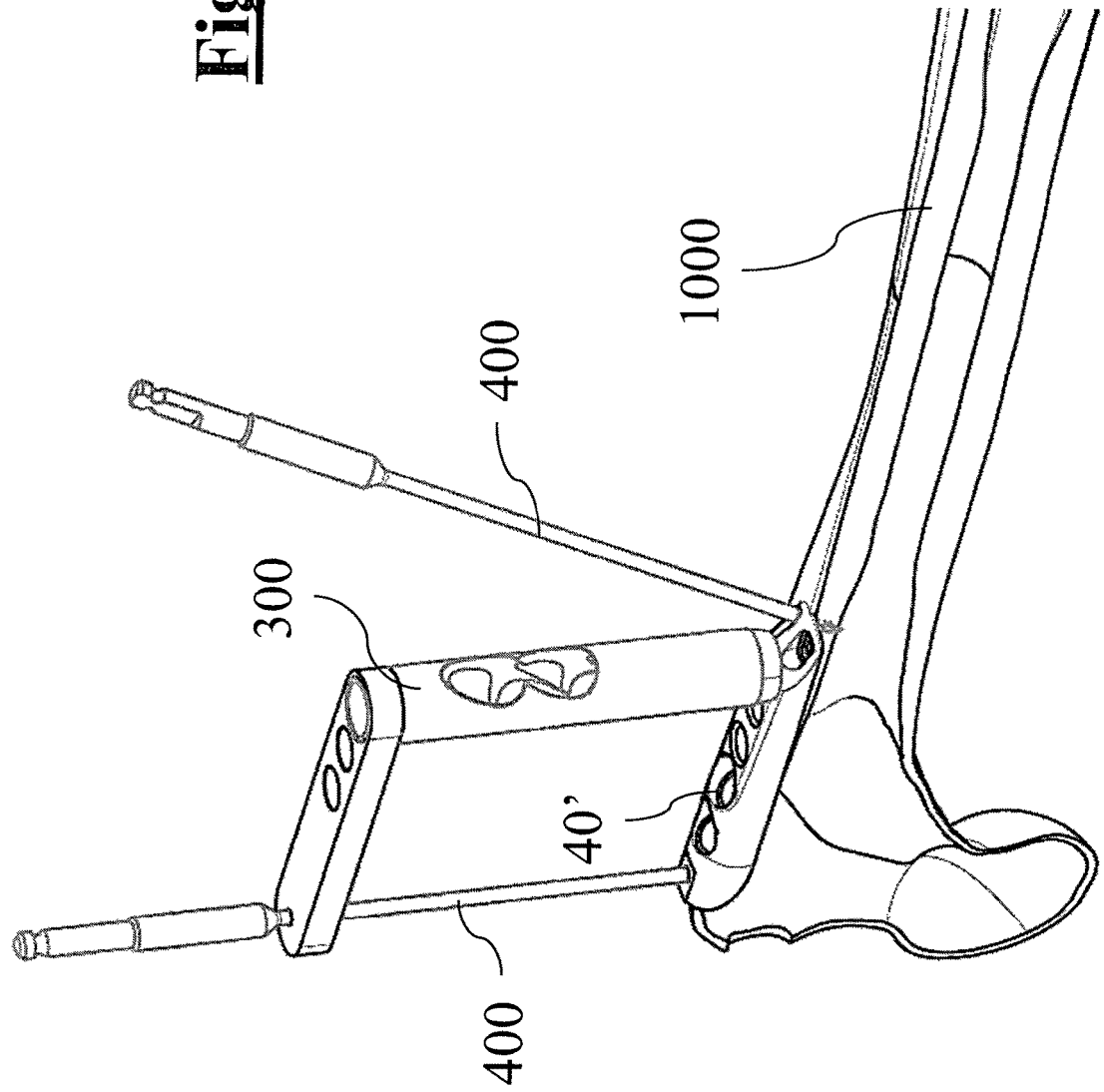
Figure 24:
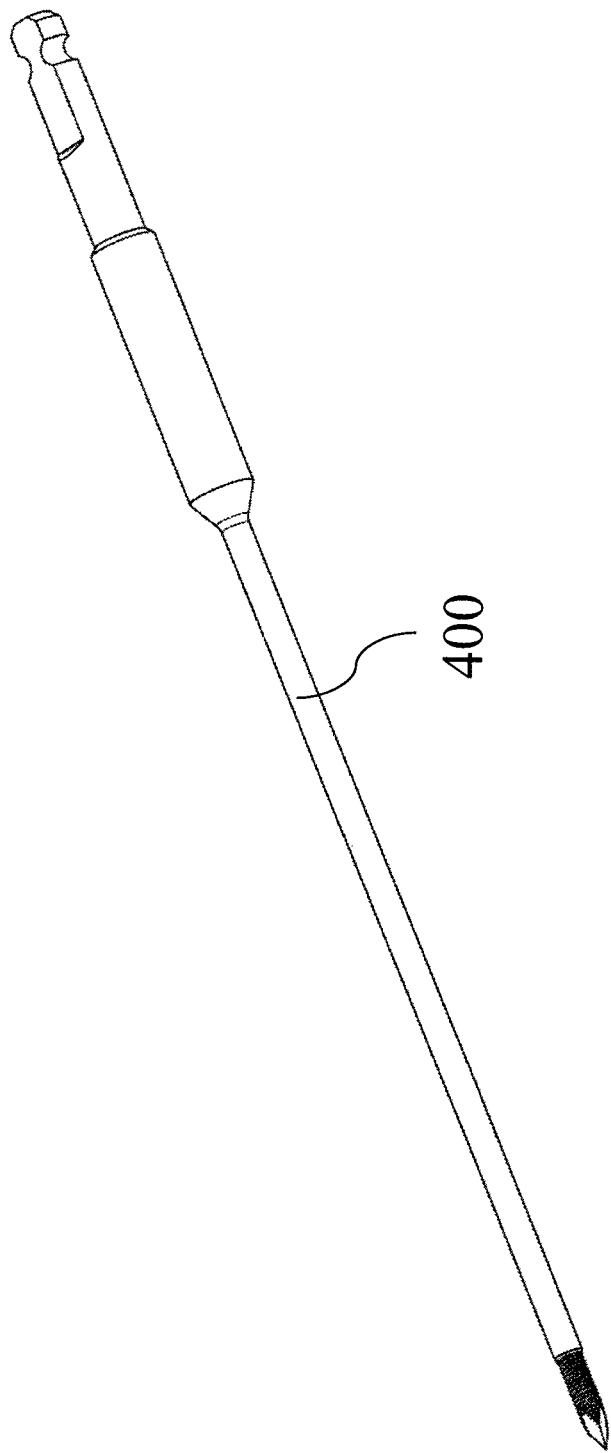

In a second step of the method, illustrated in FIG. 14, the position of the bone plate 40' is stabilized by means of threaded wires 400, one of which is individually illustrated in FIG. 24.

Threaded wires 400 are inserted in peripheral slots of the plate 40' and have a function of stabilizing the element only temporarily.

Figure 15:
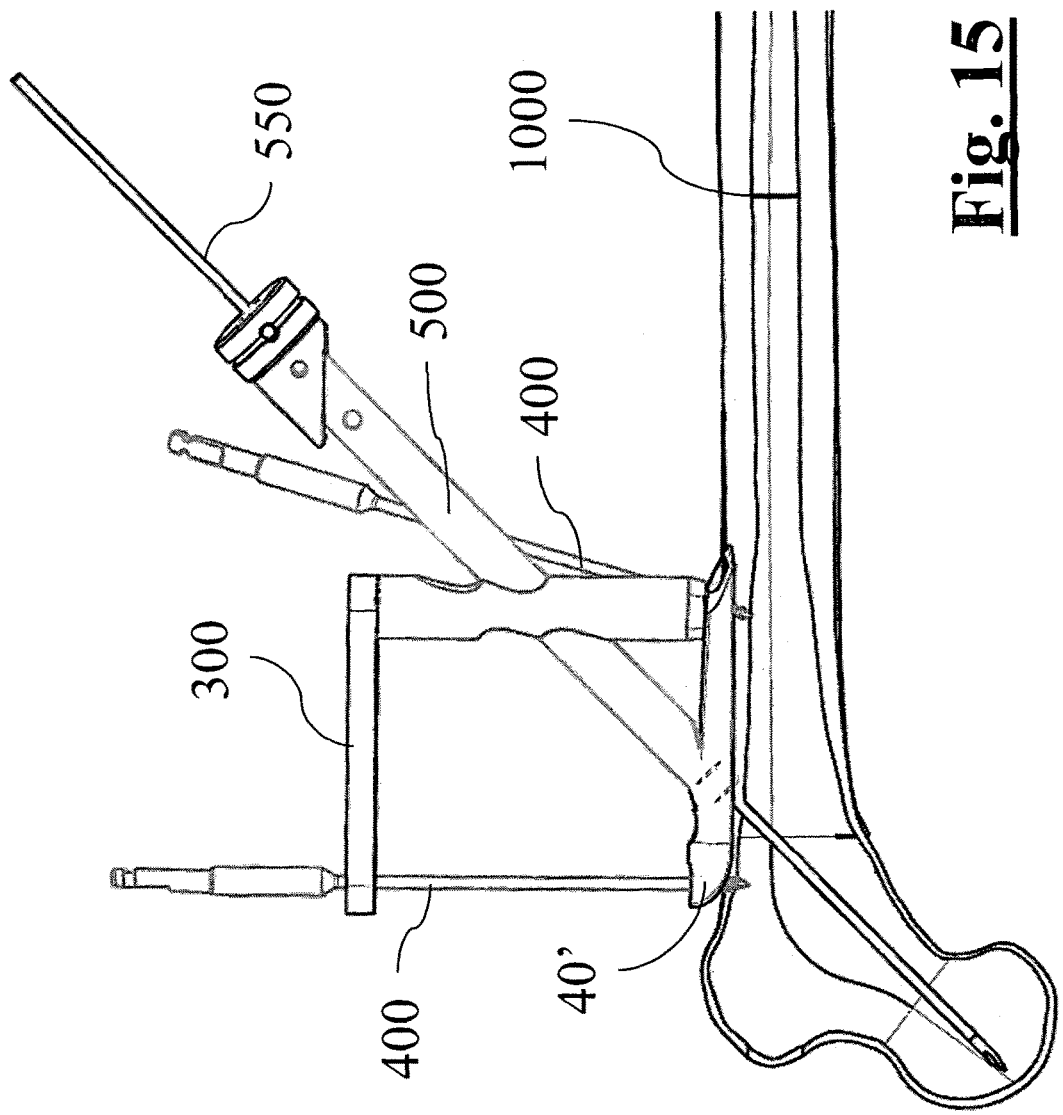
Figure 23:
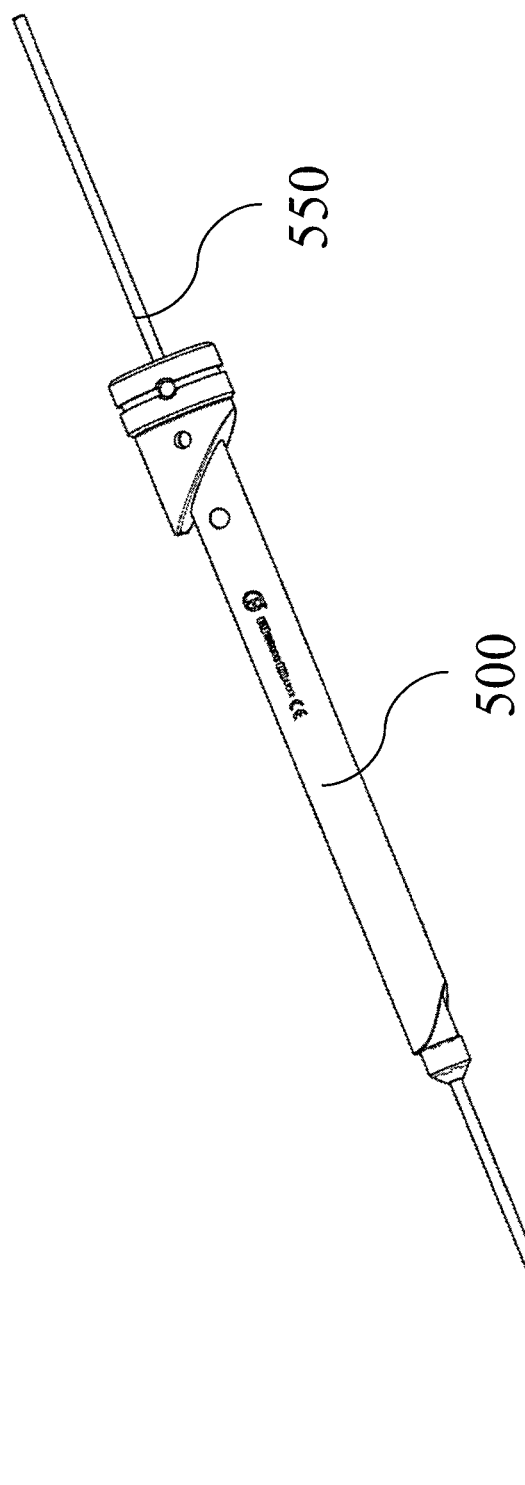

In a third step of the method, illustrated in FIG. 15, the guide wire 550 is inserted, which will serve to direct the bone screw assembly 100. The guide wire 550, which reaches in the present example the femur acetabular head, is inserted by means of a second surgical guide 500, individually illustrated in FIG. 23, which rests on the previously-positioned first surgical guide 300.

The second surgical guide 300 is then removed.

Figure 16:
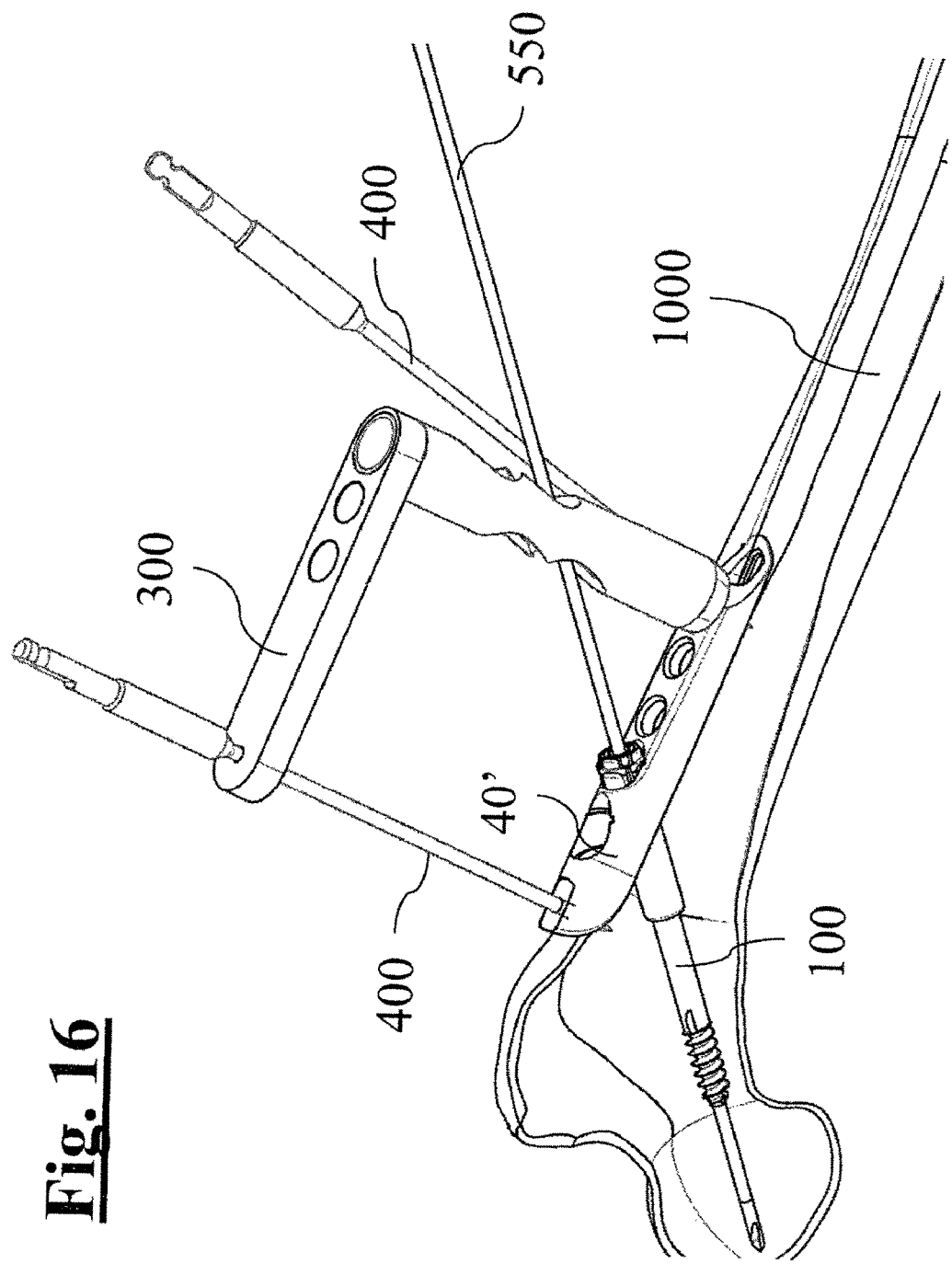

In a fourth step of the method, illustrated in FIG. 16, the endosseous screw assembly 100 is inserted in position by means of the previously-implanted guide wire 550.

Figure 17:
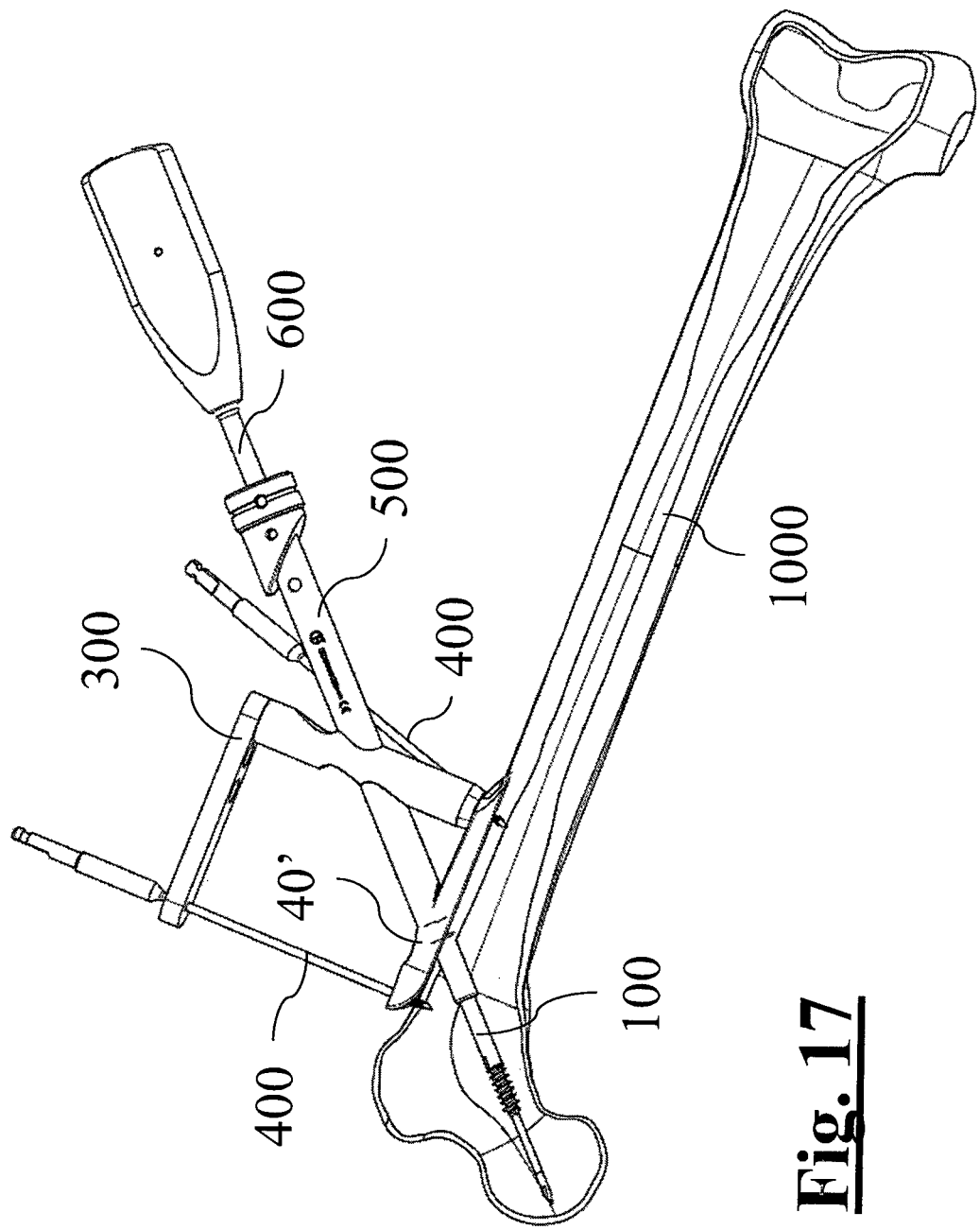
Figure 22:
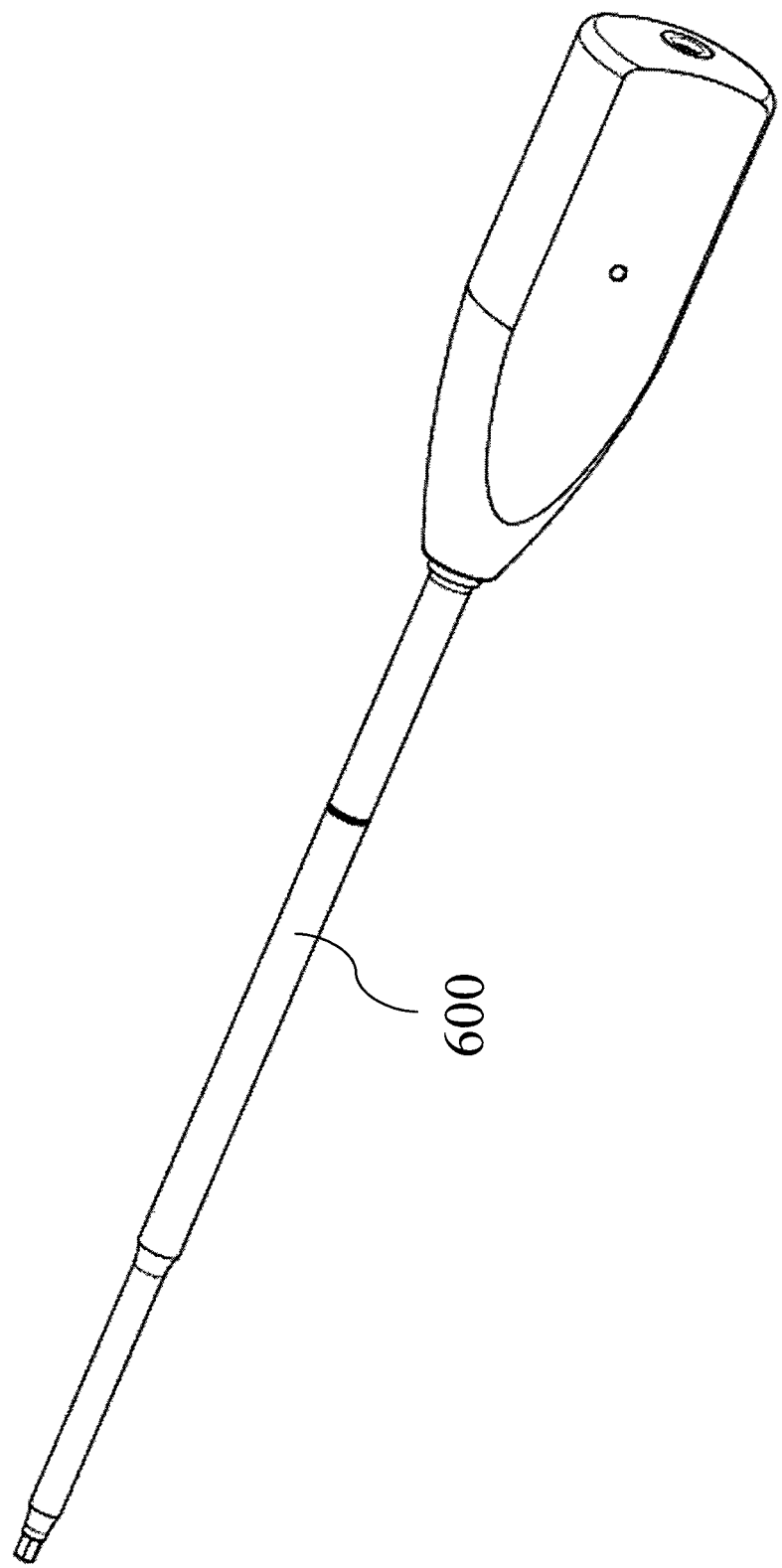

In a fifth step of the method, illustrated in FIG. 17, the previously-inserted endosseous screw assembly 100 is correctly stabilized by using a screwdriver 600, individually illustrated in FIG. 22.

It must be noted that, in order to correctly guide the screwdriver 600, the second surgical guide 500 can be used again.

During the screwing step, the threaded portion of the rod 1 digs into the bone site of the patient defining a progressive advance of the rod itself. The rod 1 slides into the connection sleeve 3 up to reach the limit stop position defined by the axial clamp 6. Afterwards, the further rod advance drags the connection sleeve 3 therewith, which slides into the connection hole 41' up to reach the locking position in which the clutch claws 7 are snap-inserted into the groove 42', defining the stabilization of the whole system.

The above-mentioned operations are obviously repeated for the second bone screw assembly 100 to be implanted.

In order to remove a bone screw assembly 100 from the housing thereof, a radial pressure must be applied inwards on the above-defined release tabs 7b.

Figure 19:
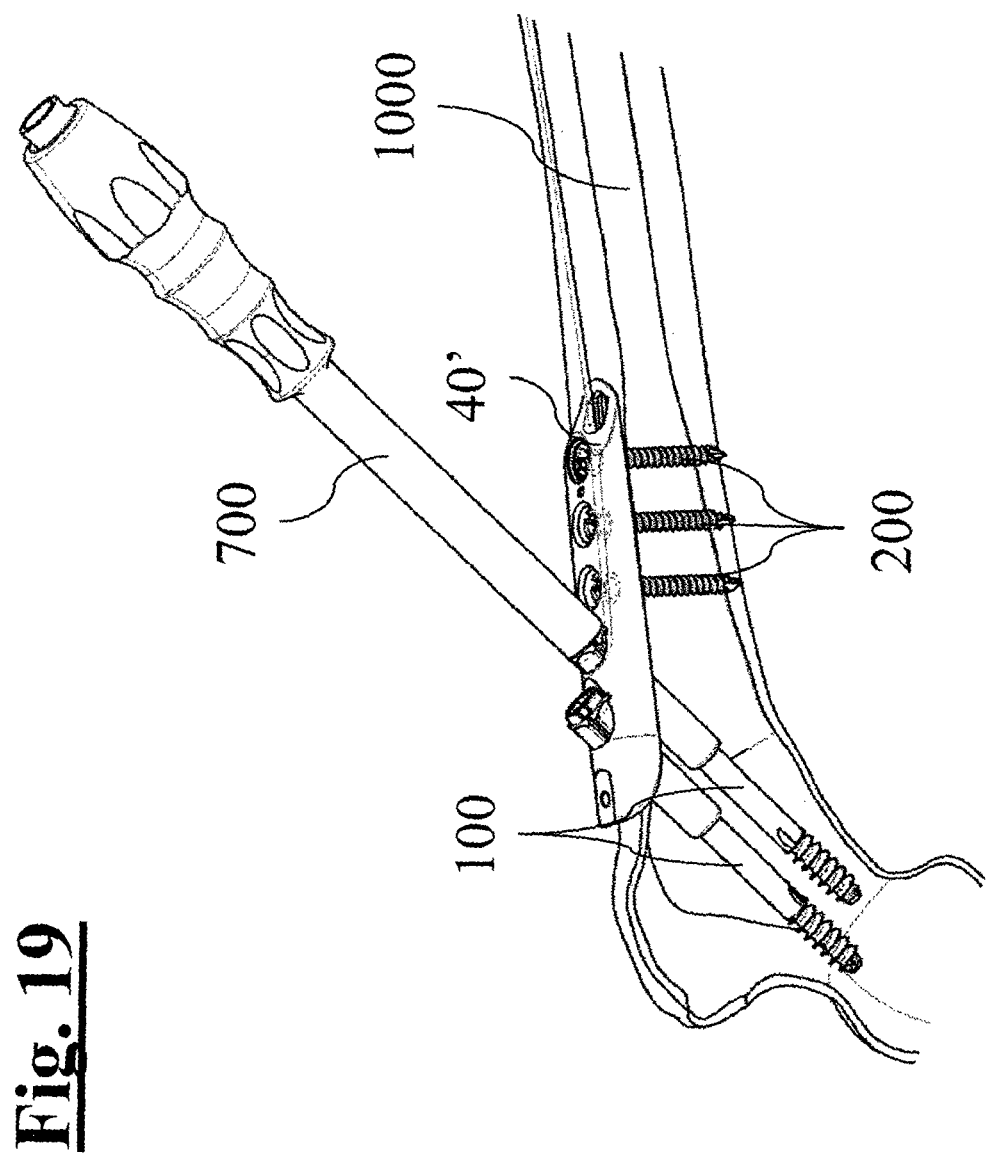
FIG. 19 shows a step of a method for removing the internal fixation system of FIG. 12.
Figure 20:
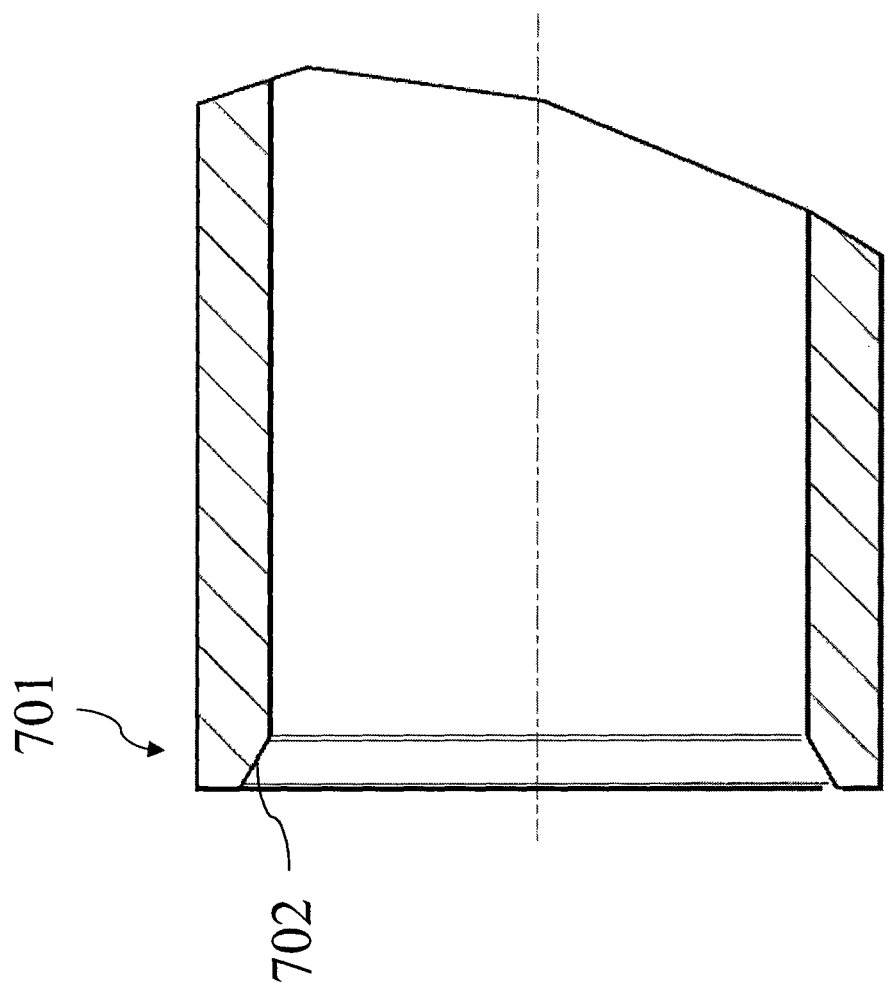
FIG. 20 shows a detail in section of an instrument used to remove an internal fixation system according to the present invention.

That operation can be performed by the release instrument 700, operatively illustrated in FIG. 19. The release instrument 700, with a tubular shape, provides a proximal mouth 701, internally equipped with a conical draft 702 which stands above the release tabs 7b bending the brackets 8 and thus disengaging the clutch claws 7 from the groove 42; 42'. The conformation of the mouth of the release instrument 700 can be appreciated in FIG. 20.

Moreover, the tubular body of the release instrument 700 can house said screwdriver 600, so that the surgeon is able to drive the rod 1 in rotation keeping the release tabs 7b lowered.

By unscrewing the rod 1, it is removed from its position dragging the connection sleeve 3 therewith, no more constrained to the internal fixation member 40, 40'.

The complete removal of the endosseous screw assembly is thus realized.

A main advantage of the invention derives from the fact that, as illustrated in the above-described surgical method, the stable connection of the endosseous screw assembly to the plate or to the endomedullary nail of the internal fixation system is obtained by using a simple screwdriver: the operations is thus extremely easy and rapid.

Similarly, the removal of the endosseous screw assembly requires the use of a simple two-stage instrument, one of which is still the screwdriver.

A further advantage of the invention derives from the high stability of the connection screw/plate or screw/nail obtained. The bending is in fact discharged by the connection of the connection sleeve with the body of the plate or of the nail, while the torsion is discharged by the simultaneous use of two coplanar screws.

Moreover, the great contact surface between the connection sleeve and the screw rod reduces the specific on-load contact pressure removing the risk of impingement present in other prior art devices.

Obviously, a person skilled in the art can bring several changes and alternatives to the above-described devices, in order to meet incidental and specific requirements, moreover all falling within the scope of protection of the invention as defined by the following claims.

The invention claimed is:

1. An internal fixation system comprising at least one endosseous screw assembly, the endosseous screw assembly comprising:
    a rod extending longitudinally and provided with at least one threaded proximal portion to allow the anchorage to a bone site of a patient;
    a connection sleeve, into which at least one portion of the rod is slidingly guided in the axial direction,
    said internal fixation system comprising at least one internal fixation member equipped with at least one connection hole arranged to house the connection sleeve of said endosseous screw assembly, said rod and said connection sleeve comprising mutual engagement means suitable for an axial constraint to the sliding of the rod into the connection sleeve, so as to define, when the threaded proximal portion advances into the bone site of a patient, a dragging of the connection sleeve into the connection hole up to reach the locking position; snap-connection means being arranged to ensure a stable connection of the connection sleeve within the connection hole, wherein said snap-connection means comprise a clutch claw and a groove, said clutch claw being arranged to snap-connect within said groove, said clutch claw and said groove being obtained on the connection sleeve and on the connection hole respectively, or vice versa, wherein said clutch claw is supported by a flexible bracket tangentially oriented compared to the rod or to the connection hole, so as to allow the clutch claw to elastically move in the radial direction, characterized in that said flexible bracket has, in correspondence with a free end thereof, a release tab axially projecting compared to the clutch claw, said release tab being lowered by a radial pressure applied inwards by the release instrument to disengage the clutch claws from the groove and the connection sleeve from the connection hole.

2. The internal fixation system according to claim 1, wherein said clutch claw has a slanting draft surface which joins the flexible bracket to the tip of the clutch claw.

3. The internal fixation system according to claim 1, wherein the flexible bracket and the related clutch claws are a plurality, circumferentially arranged around an end portion of the connection sleeve; the groove being obtained on the connection hole.

4. The internal fixation system according to claim 1, wherein said connection hole has following portions of different diameter, the connection sleeve having externally a proximal cylindrical portion and a distal collar; said proximal cylindrical portion being slidingly guided into the smaller diameter portion of the connection hole, the snap-connection means being arranged in correspondence with the greater diameter portion of the connection hole and of the distal collar of the connection sleeve.

5. The internal fixation system according to claim 4, wherein the following portions of different diameter of the connection hole define a shoulder, said distal collar abutting against said shoulder in the locking position of the connection sleeve.

6. The internal fixation system according to claim 1, comprising at least two endosseous screw assemblies arranged to be fixed parallel to each other into two corresponding connection holes of the internal fixation member.

7. The internal fixation system according to claim 1, wherein said internal fixation member is an endomedullary nail or a bone plate.

8. The internal fixation system according to claim 1, wherein said rod provides, in correspondence with the distal end thereof: a sunken housing to allow the connection with a screwing instrument; and an internal thread, which allows the possible connection of a syringe, a piston or a screw for the removal.

9. The internal fixation system according to claim 1, wherein said rod provides an axial passage connecting a distal opening to a proximal opening of the rod.

10. The internal fixation system according to claim 9, wherein said rod comprises at least one radial hole which put the axial passage in communication with the external surface of the threaded proximal portion.

* * * * *